(12) United States Patent
Sasaki et al.

(10) Patent No.: US 12,109,333 B2
(45) Date of Patent: Oct. 8, 2024

(54) BIOABSORBABLE STENT

(71) Applicants: Japan Medical Device Technology Co., LTD., Kumamoto (JP); FUJI LIGHT METAL CO., LTD., Kumamoto (JP)

(72) Inventors: Makoto Sasaki, Kumamoto (JP); Yuki Koga, Kumamoto (JP); Yuki Okazawa, Kumamoto (JP); Hironori Ueda, Kumamoto (JP); Masashi Inoue, Kumamoto (JP); Shuzo Yamashita, Kumamoto (JP)

(73) Assignees: Japan Medical Device Technology Co., LTD., Kumamoto (JP); FUJI LIGHT METAL CO., LTD., Kumamoto (JP)

( * ) Notice: Subject to any disclaimer, the term of this patent is extended or adjusted under 35 U.S.C. 154(b) by 1057 days.

(21) Appl. No.: 17/024,262

(22) Filed: Sep. 17, 2020

(65) Prior Publication Data
US 2021/0001013 A1    Jan. 7, 2021

Related U.S. Application Data

(63) Continuation of application No. PCT/JP2019/011667, filed on Mar. 20, 2019.

(30) Foreign Application Priority Data

Mar. 22, 2018  (JP) ................................ 2018-054300
Jul. 31, 2018   (JP) ................................ 2018-144220

(51) Int. Cl.
*A61L 31/02*      (2006.01)
*A61F 2/82*       (2013.01)
(Continued)

(52) U.S. Cl.
CPC .............. *A61L 31/022* (2013.01); *A61F 2/82* (2013.01); *A61L 31/088* (2013.01); *A61L 31/10* (2013.01);
(Continued)

(58) Field of Classification Search
CPC ........ A61F 2/82–945; A61F 2/24–2424; A61F 2210/0004; A61L 31/148; A61L 31/022
See application file for complete search history.

(56) References Cited

U.S. PATENT DOCUMENTS

| 5,342,576 A | 8/1994 | Whitehead |
| 9,254,350 B2 | 2/2016 | Udipi et al. |
(Continued)

FOREIGN PATENT DOCUMENTS

| CN | 101468216 A | 7/2009 |
| CN | 101629260 A | 1/2010 |
(Continued)

OTHER PUBLICATIONS

E. J. Laurilliard, K. L. Lee and J. A. Cooper, "Characterization and evaluation of fabricated poly(L-lactic) acid core fibers for ligament fascicle development," 2015 41st Annual Northeast Biomedical Engineering Conference (NEBEC), Troy, NY, USA, 2015, pp. 1-2, doi: 10.1109/NEBEC.2015.7117108. (Year: 2015).*
(Continued)

*Primary Examiner* — Rebecca S Preston
(74) *Attorney, Agent, or Firm* — Kagan Binder, PLLC (57) ABSTRACT

Provided is a biodegradable stent comprising a magnesium alloy free of a rare earth element and aluminum. The stent comprises: a core structure comprising a magnesium alloy containing 90 wt % or more of magnesium as a main component, and zinc, zirconium, and manganese as accessary components, the magnesium alloy being free of a rare earth element and aluminum; a first corrosion resistant layer
(Continued)

formed on the core structure and containing magnesium fluoride as a main component; and a second corrosion resistant layer formed on the first corrosion resistant layer and comprising a parylene. A method for producing such a bioabsorbable stent is also provided.

10 Claims, 6 Drawing Sheets

(51) Int. Cl.
    *A61L 31/08*     (2006.01)
    *A61L 31/10*     (2006.01)
    *A61L 31/14*     (2006.01)
    *A61L 31/16*     (2006.01)
    *C08L 65/04*     (2006.01)

(52) U.S. Cl.
    CPC ............. *A61L 31/148* (2013.01); *A61L 31/16* (2013.01); *C08L 65/04* (2013.01); *A61F 2210/0004* (2013.01); *A61F 2210/0076* (2013.01); *A61F 2250/0068* (2013.01); *A61L 2300/416* (2013.01); *A61L 2420/02* (2013.01); *A61L 2420/08* (2013.01); *C08L 2201/06* (2013.01); *C08L 2203/02* (2013.01)

(56) References Cited

U.S. PATENT DOCUMENTS

| | | | |
|---|---|---|---|
| 2005/0033414 | A1 | 2/2005 | Zhang et al. |
| 2005/0043788 | A1 | 2/2005 | Luo et al. |
| 2009/0131540 | A1 | 5/2009 | Hiromoto et al. |
| 2010/0145432 | A1 | 6/2010 | Bayer et al. |
| 2010/0145436 | A1 | 6/2010 | Weber et al. |
| 2010/0161053 | A1 | 6/2010 | Bayer |
| 2010/0262228 | A1 | 10/2010 | Udipi et al. |
| 2010/0305684 | A1 | 12/2010 | Kim et al. |
| 2013/0090741 | A1 | 4/2013 | Guo et al. |
| 2013/0209195 | A1 | 8/2013 | Kuwabara et al. |
| 2014/0200652 | A1 | 7/2014 | Bayer et al. |
| 2014/0277396 | A1 | 9/2014 | Mendelson et al. |
| 2016/0022876 | A1 | 1/2016 | Imwinkelried et al. |
| 2016/0129162 | A1 | 5/2016 | Pulugurtha et al. |
| 2018/0311415 | A1* | 11/2018 | Concagh ................ A61L 31/10 |
| 2019/0343666 | A1 | 11/2019 | Sasaki et al. |
| 2020/0139017 | A1* | 5/2020 | Meyer-Kobbe ....... A61L 31/028 |
| 2021/0001013 | A1 | 1/2021 | Sasaki et al. |

FOREIGN PATENT DOCUMENTS

| | | | | |
|---|---|---|---|---|
| CN | 102387825 | A | | 3/2012 |
| CN | 104046867 | A | | 9/2014 |
| CN | 104630587 | A | | 5/2015 |
| CN | 105256213 | A | * | 1/2016 ............. C22C 23/04 |
| CN | 107385419 | A | | 11/2017 |
| CN | 104498790 | A | | 4/2018 |
| EP | 0482947 | A1 | | 4/1992 |
| GB | 851871 | A | | 10/1960 |
| JP | 3518704 | B1 | | 12/1960 |
| JP | 2004183062 | A | | 7/2004 |
| JP | 2010013725 | A | | 1/2010 |
| JP | 2012082474 | A | | 4/2012 |
| JP | 2005-531391 | A | | 12/2014 |
| JP | 2014-534841 | A | | 12/2014 |
| WO | 2007108450 | A1 | | 9/2007 |
| WO | 2010025078 | A1 | | 3/2010 |
| WO | 2010117537 | A2 | | 10/2010 |
| WO | 2013052856 | A2 | | 4/2013 |
| WO | 2018122418 | A1 | | 7/2018 |
| WO | 2018139647 | A1 | | 8/2018 |

OTHER PUBLICATIONS

Machine translation of CN105256213A, accessed from Espacenet, pp. 1-6, accessed Nov. 16, 2023. https://worldwide.espacenet.com/patent/search/family/055096139/publication/CN105256213A?q=cn105256213A (Year: 2023).*
Chinese Office Action, and English Translation therefor, for Chinese Application No. 202111300689.6, mailed May 25, 2022, (18 pages).
Decision on Rejection, and English Translation thereof, for Chinese Application No. 201780082913.4, mailed Aug. 31, 2021, (12 pages).
Indian Office Action for Indian Application No. 201917027629, mailed Oct. 27, 2021, (6 pages).
"Microstructure and properties", retrieved from https://www.researchgate.net/publication/282288987_Microstructureand_properties_of_Mg-sZn-08Zr-xMn_alloy on Nov. 23, 2021, (4 pages).
Notice of Allowance and Issue Fee Due, U.S. Appl. No. 16/506,298 Mailed Oct. 1, 2021, (12 pages).
Translation of International Preliminary Amendment Report on Patentability for International Application No. PCT/JP2019/011667, mailed Oct. 1, 2020, (9 pages).
Indian Office Action for Indian Application No. 202017042569, mailed Sep. 22, 2022, (6 pages).
Communication Pursuant to Article 94(3) EPC for European Application No. 18744765.1, mailed Oct. 22, 2022, (8 pages).
E-Space net English Abstract and machine translation for CN104498790A.
Database Compendex (Online), "Microstructure and properties of Mg—3Zn—0.8Zr—xMn alloy", Database accession No. E20151300692382, Engineering Information, Inc., New York, NY, US, vol. 36, No. 2, pp. 27-31, Feb. 25, 2015, (1 page).
Agarwal et al., "Biodegradable magnesium alloys for orthopaedic applications: A review on corrosion, biocompatibility and surface modifications", Materials Science and Engineering: C, vol. 68, pp. 948-963, 2016, (16 pages).
First Chinese Office Action, and English Translation thereof, for Chinese Application No. 201980005605.0, mailed Dec. 12, 2018, (15 pages).
Gui et al., "Mechanical and corrosion properties of Mg—Gd—Zn—Zr—Mn biodegradable alloy by hot extrusion", Journal of Alloys and Compounds, vol. 685, ISSN: 0925-8388, pp. 222-230, 2016, (9 pages).
E-Space English Abstract for CN101468216A.
E-Space English Abstract for CN101629260A.
E-Space English Abstract for CN104046867A.
E-Space English Abstract for CN104630587A.
E-Space English Abstract for CN105256213A.
E-Space English Abstract for CN107385419A.
E-Space English Abstract for JP3518704B1.
E-Space English Abstract for JP2004183062A.
E-Space English Abstract for JP2010013725A.
E-Space English Abstract for JP2012082474A.
E-Space English Abstract for WO2007108450A1.
E-Space English Abstract for CN102387825A.
Notice of Reasons for Refusal, and English Translation therefor, for Japanese Application No. 2020-036796 mailed Jan. 31, 2023 (6 pages).
Chinese Office action, and English Translation therefor, for Chinese Application No. 202111300689.6 mailed Dec. 15, 2022 (16 pages).
Kowalski et al., "Ultrafine grained Mg—1Zn—1Mn—0.3Zr alloy and its corrosion behaviour," Journal of Achievements in Materials and Manufacturing Engineering, vol. 74, Isse. 2, pp. 55-59, 2016, (7 pages).
Decision of Refusal, and English Translation therefor, for Chinese Application No. 202111300689.6, mailed Apr. 21, 2023 (18 pages).
Hearing Notice for Indian Application No. 202017042569 mailed May 23, 2023 (3 pages).
Meng ShuKun, "Progress of Chinese Magnesium Industry," Metallurgical Industry Publishing House, vol. 1, p. 109, Sep. 30, 2012 (92 pages).
Mutlu, "Production and fluoride treatment of Mg—Ca—Zn—Co alloy foam for tissue engineering applications," Transactions of Nonferrous Metals Society of China, 28(1), pp. 114-124, 2018 (11 pages).
Decision on Rejection, and English Translation thereof, for Chinese Application No. 201980005605.0, mailed Aug. 4, 2021, (10 pages).

(56) References Cited

OTHER PUBLICATIONS

Second Chinese Office Action, and English Translation thereof, for Chinese Application No. 201980005605.0, mailed May 17, 2021, (17 pages).
Second Chinese Office Action, and English Translation thereof, for Chinese Application No. 201780082913.4 mailed Apr. 25, 2021, (12 pages).
Final Office Action for U.S. Appl. No. 16/506,298, mailed May 17, 2021, (30 pages).
International Search Report, and English Translation Thereof, for International Application No. PCT/JP2019/011667, mailed May 21, 2019, (4 pages).
Liu et al., "Multifunctional MgF2/polydopamine coating on Mg alloy for vascular stent application", Journal of Materials Science and Technology, vol. 31, ISSN: 1005-0302, pp. 733-743, 2015, (pages).
Kubota, "Properties of Magnesium Alloys & Their Technology", Journal of the Surface Finishing Society of Japan, vol. 53, No. 3, pp. 8-11, 2002, with machine English translation, (7 pages).
Notification of Reasons for Refusal, and English Translation Thereof, for Japanese Application No. 2019-552935, mailed Nov. 12, 2019, (9 pages).
Decision to Grant a Patent, and English Translation Thereof, for Japanese Application No. 2019-552935, mailed Feb. 4, 2020, (5 pages).
English Abstract for JP2014-534841A.
English Abstract for JP2005-531391A.
English Abstract for WO2018139647A1.
English Abstract for WO2018122418A1.

* cited by examiner

Fig. 18

BIOABSORBABLE STENT

CROSS REFERENCE TO THE RELATED APPLICATION

This application is a continuation application, under 35 U.S.C. § 111(a), of international application No. PCT/JP2019/011667, filed Mar. 20, 2019, which claims priority to Japanese patent application Nos. 2018-054300 and 2018-144220 filed Mar. 22, 2018 and Jul. 31, 2018, respectively, the entire disclosures of which are herein incorporated by reference as a part of this application.

BACKGROUND OF THE INVENTION

Field of the Invention

The present invention relates to a bioabsorbable stent configured to be implanted in a stenosis part or an occlusion part in lumen of living body, especially in the coronary arteries, so as to keep the inserted part open, and to be gradually degraded in the living body.

Description of Related Art

Ischemic heart disease (such as myocardial infarction and angina) caused by stenosis or occlusion of coronary arteries is a serious disease that interferes with supply of blood (nutrition, oxygen, etc.) to the myocardium and is the second leading cause of deaths in Japan. Recently, a minimally invasive surgical procedure using a catheter (percutaneous coronary angioplasty) has become common as a treatment for the disease, instead of a surgical operation with thoracic incision (coronary artery bypass surgery). Among others, coronary stent implantation is considered to be the most effective treatment because of the lower incidence of recurrent stenosis (restenosis) than that caused by conventional balloon plasty.

However, even though use of coronary stents has now become common, there are still many cases of long-term complications after surgery. This is due to continuous mechanical and chemical stimulus to the inner walls of the blood vessels caused by stents which contain a cobalt-chromium alloy or stainless steel as a base material. The stent remains in the affected sites after implantation thereto while expanding the inner walls of the blood vessels, so that the stents impede natural vasomotion (pulsation) and continuously give mechanical and chemical stimulus to the inner walls of the blood vessels. In the medical field, as a novel medical device that can solve these problems, there is an increasing expectation for a bioabsorbable stent that has safety and efficacy for treatment of ischemic heart disease as well as enables recovery of vasomotion as the long-term results after surgery. In recent years, bioabsorbable stents have been referred to as bioabsorbable scaffolds so that the term "bioabsorbable stent" as used herein also embraces the meaning of a bioabsorbable scaffold.

Since the bioabsorbable stent has an innovative function of gradually degrading after it is used for treatment of inserted affected area, the bioabsorbable stent is considered to be best choice for eliminating such stimuli soon and restoring normal vasomotion in the affected area. This function is also advantageous for shortening the period of taking antiplatelet drugs to prevent complications and for providing more options for postoperative retreatment.

A bare metal stent containing a bioabsorbable magnesium alloy as a base material cannot be practically applied because the bare metal stent has a problem that where the stent is expanded in an aqueous solution, the stent is decomposed (corroded) on the entire surface thereof on which water molecules come into contact so that mechanical strength of the stent is immediately impaired. Considering that a stent must maintain a sufficient vascular support force (radial force) for 3 to 6 months after stent implantation, as the magnesium alloy has a considerably higher rate of degradation in the living environment when compared with that of polylactic acid, it cannot be said that the bare metal stent has suitable characteristics.

In Patent Document 1 (US 2016/0129162) disclosing a biodegradable magnesium stent, a magnesium-alloy (AE42) base material (biodegradable metal) containing aluminum and a rare earth metal is used in both Example 1 and Example 2, which disclose preferred aspects. Patent Document 1 also discloses, as a method for suppressing corrosion of the magnesium alloy by a waterproof barrier, a processing method including: forming a magnesium fluoride layer on the surface of the base material; and further forming a chemical conversion coating layer [layers of aluminum oxide and a poly(aluminum polyethylene glycol), i.e., alucone] on the magnesium fluoride layer because the magnesium fluoride layer alone cannot sufficiently delay corrosion of the magnesium alloy.

Patent Document 2 (US 2014/0277396) disclosing a biodegradable magnesium stent, describes: forming a hydrothermal conversion film containing hydrated magnesium oxide or magnesium hydroxide on a magnesium alloy; and coating the film with a non-biodegradable polymer (a parylene, a polymethacrylate, or a polyurethane) in order to delay corrosion of the magnesium-alloy (AE42) base material (biodegradable metal) containing aluminum and a rare earth metal.

CONVENTIONAL ART DOCUMENT

Patent Document

[Patent Document 1] US 2016/0129162
[Patent Document 2] US 2014/0277396

SUMMARY OF THE INVENTION

Problems to be Solved by the Invention

In Patent Document 1, an alloy (AE42) containing aluminum and a rare earth metal is used as a magnesium alloy (Example 1 and Example 2), a magnesium fluoride layer is formed on a surface of the magnesium alloy as a barrier layer for delaying corrosion of the magnesium alloy, and chemical conversion coating layers [layers of aluminum oxide and a poly(aluminum polyethylene glycol), i.e., alucone)] are formed thereon. In Patent Document 2, a magnesium alloy (AE42) containing aluminum and a rare earth metal is used to form a stent. However, since it is preferable to suppress use of rare earth elements and aluminum in terms of safety to the human body, it is desired to use a magnesium alloy without the rare earth elements and aluminum as well as to control corrosiveness of the magnesium alloy by a surface treatment agent without aluminum.

An object of the present invention is to provide a highly-safe bioabsorbable stent comprising a magnesium alloy and a surface treatment agent in which the magnesium alloy is free of a rare earth element and aluminum and harmless to the human body

Means for Solving the Problem

Conventional bioabsorbable stents contain a magnesium alloy containing a rare earth element(s) and/or aluminum so as to have improved strength and corrosion resistance. However, since a magnesium alloy free of rare earth elements and aluminum is expected to have a higher level of safety to the living body, the inventors of the present invention have made extensive efforts to improve corrosion resistance of a stent comprising a magnesium alloy that contains 90 wt % or more of magnesium as a main component; and zinc, zirconium, and manganese as accessary components and is free of a rare earth element(s) and aluminum.

The inventors have found that although corrosion resistance of a stent comprising a magnesium alloy free of a rare earth element and aluminum can be improved by forming a magnesium fluoride layer on the stent surface, the stent still does not have sufficient corrosion resistance such that the stent can function for a predetermined period after implantation to the body.

The inventors have made further efforts and found that a stent that has a high level of safety to the living body and a practical level of corrosion resistance can be obtained by fluorinating the surface of the magnesium stent so as to form a first corrosion resistant layer and coating the surface of the first corrosion resistant layer with a layer of parylene (which collectively refers to paraxylenes and/or derivatives thereof and, hereinafter, may also referred to as paraxylylene resin) so as to form a second corrosion resistant layer. The inventors thus achieved the present invention.

According to a first aspect of the present invention, a bioabsorbable stent comprises:
a core structure comprising a magnesium alloy containing magnesium at a content of 90 wt % or more of as a main component, and zinc, zirconium, and manganese as accessary components, the magnesium alloy being free of a rare earth element and aluminum;
a first corrosion resistant layer formed on the core structure and containing magnesium fluoride as a main component; and
a second corrosion resistant layer formed on the first corrosion resistant layer and comprising a parylene.

The content of magnesium may more preferably be 93 wt % or more and further preferably be 95 wt % or more.

According to a second aspect of the present invention, the rare earth element is at least one of Sc, Y, Dy, Sm, Ce, Gd, La, and Nd; and the magnesium alloy constituting the core structure of the stent of the present invention does not contain the rare earth element(s).

According to a third aspect of the present invention, in the magnesium alloy, unavoidable impurities selected from the group consisting of iron (Fe), nickel (Ni), cobalt (Co), and copper (Cu) may preferably be contained in a total content of 30 ppm or less.

According to a fourth aspect of the present invention, the magnesium alloy may preferably comprise 0.95 to 2.00 wt % of zinc, 0.05 to 0.80 wt % of zirconium, 0.05 to 0.40 wt % of manganese, and the balance consisting of magnesium and unavoidable impurities.

According to a fifth aspect of the present invention, the first corrosion resistant layer may preferably be formed by performing fluorination to a surface of the magnesium alloy.

According to a sixth aspect of the present invention, the first corrosion resistant layer may preferably have a layer thickness from 0.5 to 1.5 μm.

According to a seventh aspect of the present invention, the parylene layer constituting the second corrosion resistant layer may preferably comprise a parylene N (chemical formula 1 below), a parylene C (chemical formula 2 below), a parylene M (chemical formula 3 below), a parylene F (chemical formula 4 below), a parylene D (chemical formula 5 below), or a parylene HT (chemical formula 6 below).

[Chem. 1]

(1)

(2)

(3)

(4)

(5)

(6)

According to an eighth aspect of the present invention, the second corrosion resistant layer may preferably have a layer thickness from 0.05 to 1 μm.

According to a ninth aspect of the present invention, on at least a part of the second corrosion resistant layer surface, a biodegradable polymer layer may be preferably formed.

According to a tenth aspect of the present invention, the biodegradable polymer may preferably be an aliphatic polyester.

According to an eleventh aspect of the present invention, the biodegradable polymer layer may preferably contain an intimal thickening inhibitor.

According to a twelfth aspect of the present invention, the inhibitor may preferably be a limus drug.

According to a thirteenth aspect of the present invention, a method for producing a bioabsorbable stent including a core structure comprising a magnesium alloy containing 90 wt % or more of magnesium as a main component, and zinc, zirconium, and manganese as accessary components, the magnesium alloy being free of a rare earth element and aluminum, the method comprises:

preparing the core structure comprising the magnesium alloy;

electropolishing the core structure and performing fluorination to a surface of the electropolished core structure so as to form a first corrosion resistant layer containing magnesium fluoride as a main component; and vapor depositing a paraxylylene resin on the first corrosion resistant layer so as to form a second corrosion resistant layer comprising a parylene.

The present invention encompasses any combination of at least two features disclosed in the claims and/or the drawings. In particular, any combination of two or more of the appended claims should be equally construed as included within the scope of the present invention.

Effect of the Invention

According to the first aspect of the present invention, desired corrosion resistance can be imparted to a magnesium alloy constituting a stent structure by forming a first corrosion resistant layer containing magnesium fluoride as a main component on the surface of the magnesium alloy and then forming a second corrosion resistant layer comprising a parylene on the first corrosion resistant layer. The stent having the above constituents can sustain mechanical strength in an expanded state in a simulated plasma solution (EMEM+10% FBS) at 37° C. under 5% $CO_2$ atmosphere over one month. The magnesium alloy and the magnesium fluoride coating on the alloy surface can function as constituents of the stent in the living body for a predetermined period and are gradually degraded to disappear, whereas the thin parylene layer formed on the magnesium fluoride layer is embedded to the surface of the blood vessels and becomes harmless because of its small thickness, though parylene is not biodegradable.

The stent structure disclosed in Patent Document 1 may have a safety problem to the human body because the stent structure is composed of the magnesium alloy containing a rare earth metal, a corrosion resistant layer of magnesium fluoride that is formed on the surface of the magnesium alloy, and chemical conversion coating layers containing aluminum [layers of aluminum oxide and a poly(aluminum polyethylene glycol) (i.e., alucone)] that is formed the corrosion resistant layer. Patent Document 2 may also have a safety problem to the human body because the stent is composed of a magnesium alloy containing a rare earth metal. Contrarily, according to the present invention, the stent has a higher level of safety to the human body because the stent comprises a magnesium alloy free of a rare earth element and an aluminum-free corrosion resistant layer formed on the surface of magnesium alloy.

The magnesium alloy used in the first aspect of the present invention contains: 90 wt % or more of magnesium (Mg); and zinc (Zn), zirconium (Zr), and manganese (Mn) as accessary components.

The magnesium alloy used in the present invention contains Zn in a proportion of 0.95 wt % or higher and 2.0 wt % or lower so that a solid solution of Zn in Mg is formed so as to enhance the strength of the alloy, as well as Zr in a proportion of 0.05 wt % or higher and 0.80 wt % or lower so as to prevent the magnesium alloy from having coarse crystal grains. The magnesium alloy used in the present invention has a grain size distribution with an average crystal grain size from 1.0 to 3.0 μm and a standard deviation of 0.7 or lower and has excellent deformability (extensibility, ductility). The magnesium alloy contains Mn in proportion from 0.05 wt % or higher and 0.40 wt % or lower, so that the magnesium alloy provides an effect of enhancing corrosion resistance. Thanks to the above properties, the magnesium alloy used in the present invention can form a core structure of a bioabsorbable stent without a rare earth element(s) and aluminum which are often contained as accessary components of a biodegradable magnesium alloy.

In the second aspect of the present invention, the rare earth element refers to at least one of Sc, Y, Dy, Sm, Ce, Gd, La, and Nd, and the magnesium alloy used in the present invention does not contain the rare earth element(s) and aluminum.

In the third aspect of the present invention, although Fe, Ni, Co, and Cu are unavoidable impurities, it is preferable that a content of each of the unavoidable impurities is suppressed below 10 ppm, and a total content of the unavoidable impurities is suppressed to 30 ppm or lower because the unavoidable impurities have an effect of promoting corrosion of the magnesium alloy.

In the fourth aspect of the present invention, the magnesium alloy contains certain amounts of zinc, zirconium, and manganese, so that the magnesium alloy has a fine and uniform microstructure with an average crystal grain size from 1.0 to 3.0 μm, zirconium-containing precipitates each has a grain size smaller than 500 nm, and a matrix phase excluding zirconium forms an all-proportional solid solution of the Mg—Zn—Mn ternary alloy.

This alloy has a tensile strength from 230 to 380 MPa, a proof strength from 145 to 300 MPa, and a fracture elongation from 15 to 50% in accordance with JIS Z2241, and satisfies the conditions for the core structure constituting the bioabsorbable stent.

In the fifth and sixth aspects of the present invention, fluorination to the entire surface of the core structure constituting the bioabsorbable stent can enhance corrosion resistance of the magnesium-alloy core structure. The first corrosion resistant layer may preferably have a layer thickness from 0.5 μm to 1.5 μm. Although the first corrosion resistant layer preferably has a larger layer thickness in order to improve corrosion resistance such that the stent having the magnesium-alloy core structure can function in the blood vessel for a predetermined period of time, there is a limit to the layer thickness of the magnesium fluoride layer formed by fluorination, and it may be difficult to form a magnesium fluoride layer having a layer thickness exceeding 1.5 μm. Therefore, it is necessary to supplementarily impart corrosion resistance by a second corrosion resistant layer.

According to the seventh and eighth aspects of the present invention, the second corrosion resistant layer has good deformation followability because it comprises, e.g., a parylene N, a parylene C, a parylene M, a parylene F, a parylene D, or a parylene HT as mentioned above. Among these, the second corrosion resistant layer comprising a parylene C is preferable because of enhanced stretchability.

The second corrosion resistant layer may preferably have a layer thickness in a range from 0.05 to 1 μm. Since the parylene constituting the second corrosion resistant layer is not biodegradable and remains in the blood vessels, the second corrosion resistant layer is required to have a minimal thickness necessary to supplement the corrosion resistance of the first corrosion resistant layer (magnesium fluoride layer). Where the layer thickness of the second corrosion resistant layer is too small, the second corrosion resistant layer is not able to complement a shortfall in the corrosion resistance of the first corrosion resistant layer. In contrast, where the layer thickness is too large, the second corrosion resistant layer may provide a too much anticorrosive effect that influences bioabsorbability of the stent, and parylene remaining in the blood vessels could have an adverse effect on the blood vessels.

According to the ninth to twelfth aspects of the present invention, on at least a part of the second corrosion resistant layer surface, a biodegradable polymer layer may preferably be formed. The biodegradable polymer layer enables smooth insertion of the stent into blood vessels. Also, the biodegradable polymer layer may contain a drug (such as a limus type intimal thickening inhibitor).

The biodegradable polymer layer may include two layers: a first layer on the second corrosion resistant layer side and a second layer on the blood side. The second layer that comes into contact with the blood may contain a medicine.

The biodegradable polymer layer is intended to disappear from the body after a predetermined period has passed.

According to the thirteenth aspect of the present invention (method for producing a stent), an anticorrosive stent can be obtained by the following steps: electropolishing a stent structure comprising the magnesium alloy so as to make the stent surface smooth; treating the stent surface with hydrogen fluoride so as to form a magnesium fluoride layer on the stent surface; and then vapor-depositing a paraxylylene resin on the magnesium fluoride layer.

BRIEF DESCRIPTION OF THE DRAWINGS

The present invention will be more clearly understood from the following description of preferred embodiments thereof, when taken in conjunction with the accompanying drawings. However, the embodiments and the drawings are given only for the purpose of illustration and explanation, and are not to be taken as limiting the scope of the present invention in any way whatsoever, which scope is to be determined by the appended claims. In the accompanying drawings, like reference numerals are used to denote like parts throughout the several views. In the figures.

DESCRIPTION OF THE EMBODIMENTS

Basic Structure of Stent

Figure 1:
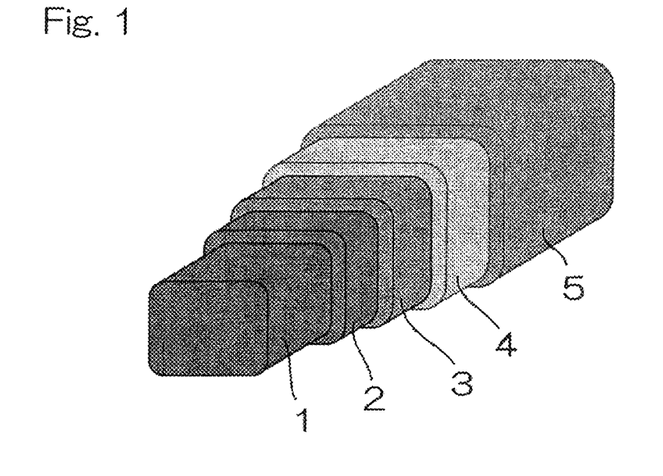
FIG. 1 shows a schematic view illustrating constituents of a stent according to the present invention.

As shown in FIG. 1, an example of a stent of the present invention comprises: a core structure 1 comprising a magnesium alloy (Mg alloy); a first corrosion resistant layer 2 formed on an entire surface of the core structure 1 and comprising magnesium fluoride ($MgF_2$) [the first corrosion resistant layer contains $Mg(OH)_2$ etc. formed by oxidation of Mg on the layer surface and thus exhibits hydrophilicity]; a second corrosion resistant layer 3 formed on the first corrosion resistant layer 2 and comprising a parylene; a biodegradable resin layer 4 formed at least a part of a surface of the second corrosion resistant layer 3; and a biodegradable resin layer 5 formed on the biodegradable resin layer 4 and containing a medicine or a drug (it should be noted that the biodegradable resin layer 4 may contain a medicine or a drug, instead of providing a biodegradable resin layer 5 containing a medicine).

The following technical elements are provided to obtain the above configuration: an element for selecting a composition of the magnesium alloy for constituting the core structure having a biodegradability and excellent deformability; an element for forming the first corrosion resistant layer containing $MgF_2$ as a main component over the entire surface of the core structure so as to control corrosion of the core structure comprising the selected magnesium alloy; an element for forming the second corrosion resistant layer comprising a parylene on the first corrosion resistant layer; and an element for forming a biodegradable resin layer coated on the core structure and containing a medicine or a drug.

Magnesium Alloy

The core structure of the stent according to the present invention comprises a bioabsorbable magnesium alloy.

In the present invention, the core structure of the stent comprises a magnesium alloy that contains 90 wt % or more of magnesium (Mg) as a main component; and zinc (Zn), zirconium (Zr), and manganese (Mn) as accessary components and is free of a rare earth element(s) and aluminum (Al).

In order to enhance safety to the human body and mechanical properties, the content of Mg may more suitably be 93 wt % or more and further suitably be 95 wt % or more.

In the present invention, the magnesium alloy does not contain a rare earth element(s). The rare earth element may refer to at least one selected from the group consisting of scandium (Sc), yttrium (Y), dysprosium (Dy), samarium (Sm), cerium (Ce), gadolinium (Gd), lantern (La), and neodymium (Nd). Absence of the rare earth element(s) and aluminum can prevent a potential harmful effect to the human body.

Accessary Component

The magnesium alloy may preferably contain 0.95 to 2.0 wt % of Zn, 0.05 to 0.80 wt % of Zr, and 0.05 to 0.40 wt % of Mn as accessary components.

Zn is added in order to enhance the strength and ductility of the alloy by forming a solid solution with Mg. A too small amount of Zn may be not preferable because of insufficient desired effect. A too large amount of Zn may be not preferable because such an amount may exceed a solid solubility limit of Zn in Mg that Zn-rich precipitates are formed, resulting in reduced corrosion resistance.

Zr hardly forms a solid solution in Mg, and forms fine precipitates, providing an effect of preventing the alloy from having coarse crystal grains. Where a too small amount of Zr is added, the effect of addition cannot be obtained. Where a too large amount of Zr is added, the amount of precipitates increases and the processability decreases, which is not preferable.

Mn allows alloy structure (crystal structure) to be extremely fine so as to have improved corrosion resistance. Where the content of Mn is too small, the desired effect cannot be obtained. Where the content of Mn is too large, plastic working of the alloy tends to decrease.

Calcium (Ca) may further be added to the above accessary components in a proportion of 0.05 wt % or more and less than 0.20 wt %. Since Ca is expected to have the effect of improving the corrosion resistance while maintaining the strength of the magnesium alloy, Ca may be added depending on needs. Where the content of Ca is too small, the effect of addition cannot be obtained. A too large content of Ca is not preferable because of a possibility of precipitate formation, making it difficult to obtain a single-phase complete solid solution.

Unavoidable Impurities

In the present invention, the magnesium alloy may contain unavoidable impurities selected from the group consisting of iron (Fe), nickel (Ni), cobalt (Co), and copper (Cu), the content of each of the unavoidable impurities preferably being lower than 10 ppm, and the total content of the unavoidable impurities preferably being 30 ppm or lower.

The contents of the unavoidable impurities are preferably controlled. Since Fe, Ni, Co, and Cu promote corrosion of the magnesium alloy, the content of each of the unavoidable impurities may be lower than 10 ppm and further preferably 5 ppm or lower. The total content of the unavoidable impurities is preferably 30 ppm or lower and further preferably lower than 10 ppm. The contents of the unavoidable impurities can be determined by, for example, ICP atomic emission spectroscopy.

Production of Magnesium Alloy

In accordance with an ordinal production method of a magnesium alloy, the magnesium alloy may be produced by throwing ground metals or alloys of Mg, Zn, Zr, Mn and, if needed, Ca into a crucible, melting the ground metals and/or alloys in the crucible at a temperature from 650 to 800° C., and casting the molten alloy. Where necessary, the cast alloy may be subjected to solution heat treatment. The ground metals do not contain the rare earth element(s) and aluminum. It is possible to suppress the amounts of Fe, Ni, and Cu in the impurities by the use of high purity ground metals. Fe, Ni, and Co in the impurities of the molten alloy may be removed by de-ironing treatment. In addition, or alternatively, it is possible to use ground metals produced by distillation refining.

Structure of Metal and Mechanical Properties

The magnesium alloy used in the present invention can have a fine and uniform structure in terms of a grain size distribution with an average crystal grain size from 1.0 to 3.0 μm (preferably from 1.0 to 2.0 μm) and a standard deviation of 0.7 or lower (preferably from 0.5 to 0.7), thanks to the composition as described above and controlled production method. Fine precipitates containing Zr may each have a particle diameter smaller than 500 nm (preferably smaller than 100 nm). A matrix phase excluding the Zr-precipitates may preferably be an all-proportional solid solution of the Mg—Zn—Mn ternary alloy.

The magnesium alloy used in the present invention preferably has mechanical properties such as a tensile strength from 230 to 380 MPa (preferably from 250 to 300 MPa), a proof strength from 145 to 220 MPa, and a fracture elongation from 15 to 50% (preferably from 25 to 40%) when measured in accordance with JIS Z2241. In particular, the magnesium alloy further preferably has a tensile strength exceeding 280 MPa and a fracture elongation exceeding 30%.

Shape of Stent Scaffold

The ingots prepared in the above-described manner are subjected to hot extrusion to produce a magnesium alloy tubular material, and the thus-obtained magnesium alloy tubular material is laser-processed to form a stent scaffold (core structure).

The stent of the present invention may be formed into various scaffold shapes including conventional ones. For example, the stent may have the scaffold shape shown in FIG. 2 or FIG. 3.

Electropolishing

As a pretreatment for forming a corrosion-resistant layer having a smooth surface, a preferable method of producing a core structure having an arbitrary size includes: connecting a laser-processed stent scaffold and a metal plate to an anode and a cathode, respectively, via a direct current (DC) power source in an electrolytic solution; and applying a voltage to them so as to electropolish the stent scaffold on the side of the anode.

Formation of First Corrosion Resistant Layer

In order to form a corrosion resistant layer having a smooth surface, the mirror-finished core structure by electropolishing is subjected to fluorination. As long as a $MgF_2$ layer can be formed, the condition of fluorination is not particularly limited. For example, the core structure may be immersed in a treatment liquid such as an aqueous solution of hydrofluoric acid (HF) to carry out fluorination. It is preferable to shake the core structure at a speed of, for example, 50 to 200 rpm (preferably 80 to 150 rpm) during immersion. Then, the core structure on the surface of which the $MgF_2$ layer is formed is taken out and sufficiently washed with a cleaning solution (for example, acetone and water). The core structure is, for example, washed by ultrasonic cleaning. Where the core structure is dried after cleaning, the core structure is preferably dried at a temperature from 50 to 60° C. under reduced pressure for 24 hours or longer.

Feature of First Corrosion Resistant Layer

The first corrosion resistant layer of the stent according to the present invention contains magnesium fluoride as a main component. For example, the first corrosion resistant layer may contain 90% or more of $MgF_2$ as a main component. The first corrosion resistant layer may also contain oxides and hydroxides such as MgO and Mg(OH)$_2$ as accessary components. It should be noted that the first corrosion resistant layer may also contain oxides and hydroxides of metals other than magnesium which constitute the stent.

Layer Thickness of First Corrosion Resistant Layer

The first corrosion resistant layer of the stent according to the present invention suitably has a layer thickness of 0.5 μm or larger in order to exhibit corrosion resistance and a layer thickness of 1.5 μm or smaller in order to exhibit deformation followability. A layer thickness exceeding 1.5 μm may be avoided because too high corrosion resistance impairs bioabsorbability.

Feature and Layer Thickness of Second Corrosion Resistant Layer

In the present invention, a thin second corrosion resistant layer comprising a parylene and having a thickness from 0.05 to 1 μm (preferably from 0.08 to 0.8 μm) is formed on the first corrosion resistant layer so as to remarkably improve corrosion resistance of the magnesium alloy without impairing bioabsorbability. Where the second corrosion resistant layer is too thin, the anticorrosion effect tends to be insufficient; where the second corrosion resistant layer is too thick, bioabsorbability tends to be impaired.

Parylene collectively refers to paraxylylenes and derivatives thereof. Examples of parylenes may include: a parylene N having no functional group in the aromatic ring [the following formula (1)], a parylene C in which one of the hydrogens in the aromatic ring is substituted with chlorine [the following formula (2)], a parylene M in which one of the hydrogens in the aromatic ring is substituted with a methyl group [the following formula (3)], a parylene F in which one of the methylene groups of the parylene M is fluorinated [the following formula (4)], a parylene D in which hydrogens at the 2,5-positions of the aromatic ring of the parylene N are replaced by chlorine [the following formula (5)], and a parylene HT in which both the methylene groups of the parylene N are fluorinated [the following formula (6)]. These parylenes are commercially available; for example, a parylene N and a parylene C can be obtained from Dai San Kasei Co., Ltd.

[Chem. 2]

(1)

(2)

(3)

(4)

(5)

(6)

The second corrosion resistant layer comprising a parylene is typically formed by CVD process. The CVD process of parylene itself is known, and the process includes: in a device system having a vaporization furnace, a decomposition furnace and a vapor deposition chamber, (a) subjecting the device system to be vacuumed to have a pressure inside the device system of approximately 1 to 4 Pa using a vacuum pump; (b) heating dimers in the vaporization furnace to a temperature of 100 to 180° C. so as to sublimate the dimers; (c) passing the dimers through the decomposition furnace pipe at 650 to 700° C. so as to convert the dimers into monomers; and (d) polymerizing the monomers to a parylene in the vapor deposition chamber to be deposited on the surface of a first corrosion resistant layer at a predetermined thickness so as to form a second corrosion resistant layer.

Biodegradable Resin Layer

In the stent of the present invention, a cover layer comprising a biodegradable polymer and an intimal thickening inhibitor may be formed on the entirety or a part of a surface of the second corrosion resistant layer. Examples of the biodegradable polymers may include polyesters, such as a poly-L-lactic acid (PLLA), a poly-D,L-lactic acid (PDLLA), a poly(lactic acid-glycolic acid) (PLGA), a polyglycolic acid (PGA), a polycaprolactone (PCL), a polylactic acid-ε-caprolactone (PLCL), a poly(glycolic acid-ε-caprolactone) (PGCL), a poly-p-dioxanone, a poly(glycolic acid-trimethylene carbonate), a poly-β-hydroxybutyric acid, and others.

Intimal Thickening Inhibitor

Examples of the intimal thickening inhibitor may include sirolimus, everolimus, biolimus A9, zotarolimus, paclitaxel, etc.

Performance of Stent

The stent on which the corrosion resistant layer having the smooth surface is formed as described above can have a significantly suppressed temporal reduction of a radial force in a simulated plasma solution (EMEM+10% FBS) at 37° C. under 5% CO$_2$ atmosphere as well as in pig coronary arteries, when compared with a stent that does not fall within the scope of the present invention or a stent without a corrosion resistant layer (core structure alone) (see Examples and Comparative Examples below).

EXAMPLE

Hereinafter, the present invention will be specifically described with reference to Examples. The present invention, however, is not limited to the following Examples.

Figure 2:
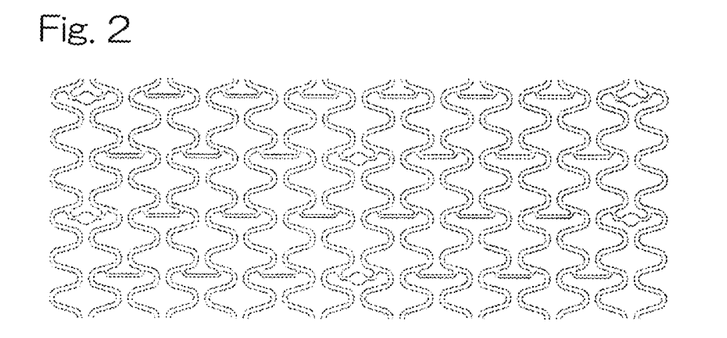
FIG. 2 shows a plan view illustrating an example of a scaffold structure of a stent according to the present invention.
Figure 3:
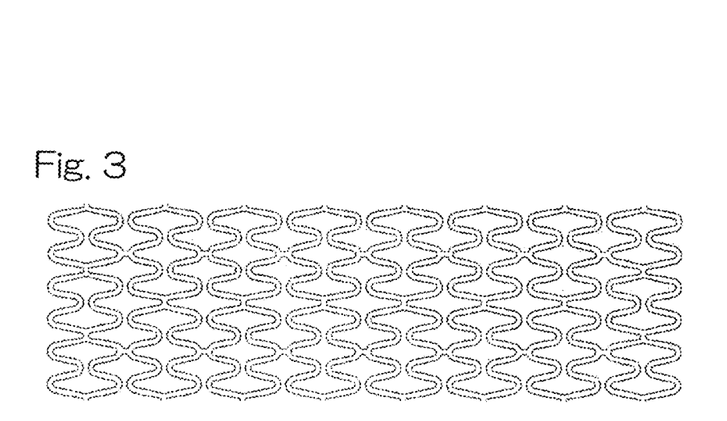
FIG. 3 shows a plan view illustrating another example of a scaffold structure of a stent according to the present invention.

Examples and Comparative Examples adopted a stent structure having the design shown in FIG. 2. It should be noted that comparable results can be obtained even where the design shown in FIG. 3 is employed.

(1) Production of Magnesium Alloy for Stent

High purity ground metals of Mg, Zn, Mn, and Zr were prepared as initial materials. Each of the metals was weighed so as to have a component concentration as described below and was thrown into a crucible. Then, at 730° C. the metals were molten with stirring, and a thus-obtained melt was cast to form ingots. The initial materials used did not contain rare earth elements or aluminum even as unavoidable impurities.

In this regard, 99.9% pure magnesium ground metal having low concentration of impurity Cu was used. De-ironing treatment was carried out in the furnace in order to remove iron and nickel from the melt.

Concentrations of impurities in the thus-obtained ingots were determined using an ICP atomic emission spectrometer (AGILENT 720 ICP-OES manufactured by AGILENT).

The ingots had the following component concentrations (wt %): Mg balance with Zn 1.5%, Mn 0.4%, and Zr 0.4%. The ingots did not contain aluminum and rare earth elements.

The ingots contained Fe, Ni, Co and Cu as unavoidable impurities at the following concentrations: Fe 5 ppm, Ni 5 ppm, Co ND: undetectable (below detection limit), and Cu 1 ppm.

(2) Production of Stent Scaffold

The magnesium alloy ingot was subjected to extrusion processing to produce a thin tube having a thickness of 150 μm (outer diameter 1.8 mm/inner diameter 1.5 mm), and the thin tube was laser-processed into the shape shown in FIG. 2 to obtain a stent scaffold.

(3) Electropolishing

The surface of the thus-obtained stent scaffold was cleaned with an acidic solution to remove oxides on the surface. Then, the stent scaffold was immersed in an electrolytic solution. The stent scaffold was connected to an anode side and a metal plate was connected to a cathode side, via a DC power source. A voltage was then applied such that the stent scaffold on the anode side was mirror-polished until the stent scaffold had a thickness of 100 μm (outer diameter 1.75 mm/inner diameter 1.55 mm) so as to make the stent surface smooth. During voltage application, the electrolytic solution was stirred with keeping a constant temperature in order to stabilize a viscous liquid layer. Also, in order to suppress bubbles generated on the cathode, the voltage was intermittently applied as appropriate. It should be noted that adherence of bubbles released from the cathode to the stent scaffold may cause poor surface precision.

(4) Test Sample

A stent sample later-described in each of the Examples and Comparative Examples was prepared from the stent scaffold. The stent sample was positioned (crimped) on a balloon attached to a distal end portion of a balloon catheter such that the stent sample had an outer diameter of 1.2 mm.

A layer thickness of a first corrosion resistant layer of a stent sample was measured in the following way. The stent sample on which the first corrosion resistant layer was formed as described in the Examples and Comparative Examples was subjected to gold sputtering and then embedded into an epoxy resin. Thereafter, the layer thickness was measured on a cut surface of the stent sample using an SEM-EDX. On the other hand, a layer thickness of a second corrosion resistant layer was measured using an ellipsometer or a spectrographic film thickness meter, from a surface of a stent sample having the second corrosion resistant layer as described in the Examples and Comparative Examples.

Evaluation of Corrosion Resistance and Deformation Followability

A surface having excellent corrosion resistance and deformation followability is capable of delaying decrease in mechanical strength associated with accelerated corrosion of a core structure in the blood vessels. Thus, corrosion resistance and deformation followability can be evaluated by determining a weight change and a radial force residual ratio of the core structure in a simulated plasma solution (EMEM+10% FRS) at 37° C. under 5% $CO_2$ atmosphere.

Evaluation of Weight Change and Radial Force Residual Ratio

Figure 4:
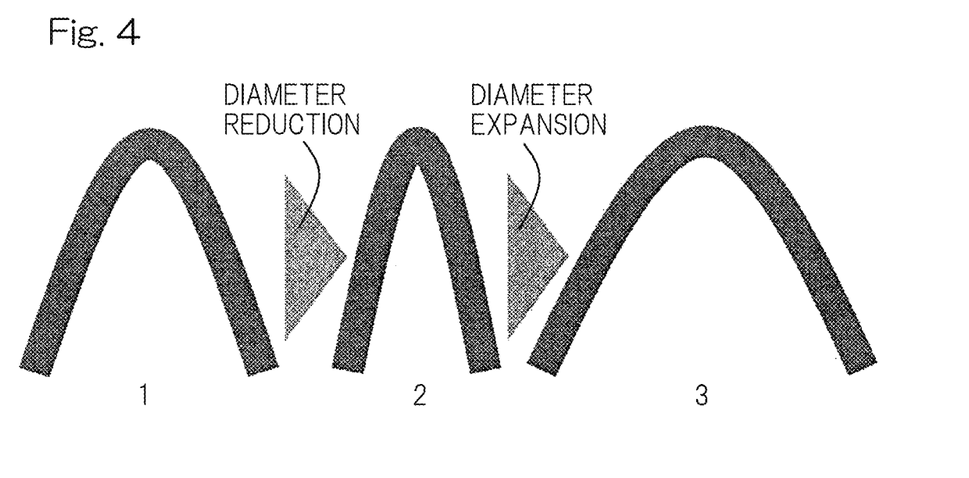
FIG. 4 shows a schematic view illustrating physical change due to diameter reduction and diameter expansion of a stent according to the present invention.
Figure 5:
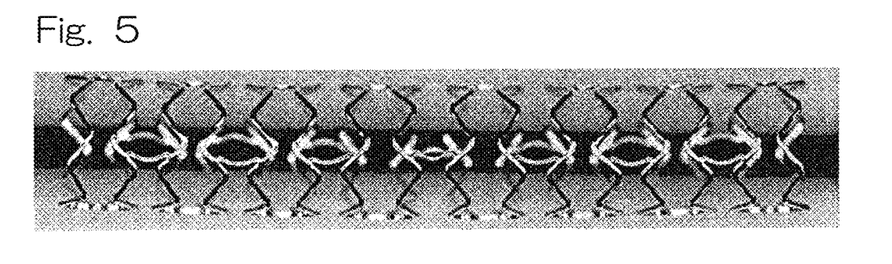
FIG. 5 shows an example of a microscopic observation image of a stent according to the present invention which is expanded to have an inner diameter of 3 mm.
Figure 6:
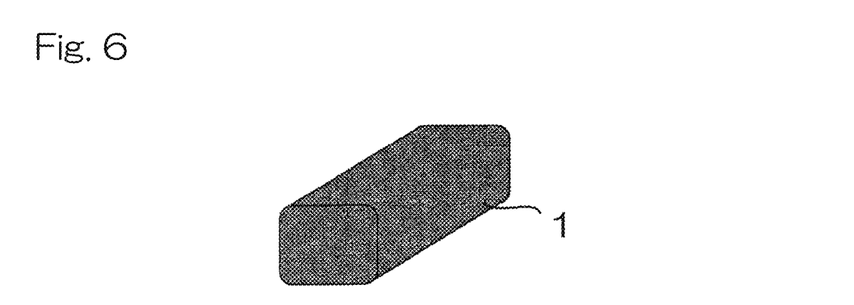
FIG. 6 shows a schematic view of a stent of Comparative Example 1.

A stent sample crimped at a balloon catheter was immersed in a 37° C. simulated plasma solution (EMEM+10% FBS) for 2 minutes, then was uniformly expanded to have an inner diameter of 3 mm (FIG. 5), and was shaken at 100 rpm with keeping immersion at 37° C. under 5% $CO_2$ atmosphere. It means that the stent at this stage was exposed to plastic elastic deformation (physical change) by crimping (reducing diameter) to a balloon catheter and stenting (expanding diameter) (FIG. 4). The sample was taken out after 28 days of immersion, and the radial force of the sample was measured. Further, the sample was cleaned ultrasonically with a chromic acid solution to completely remove corrosion products such as magnesium hydroxide, etc., and the weight change of the core structure was evaluated (n=5). As to the radial force measurement, RX550/650 (produced by Machine Solutions Inc.) was used.

Evaluation of Mg Ion Elution Rate

Each of the samples of Example 2, Comparative Example 2 and Comparative Example 3 described below was immersed and shaken in the simulated plasma solution in the same manner as described above. After 7, 14, 21 and 28 days of immersion, an amount of Mg ions eluted from the sample was measured, and an Mg ion elution rate was calculated based on the weight of the core structure before immersion (n=5). As to the Mg ion measurement, a magnesium B-test Wako (produced by Fujifilm Wako Pure Chemical Industries, Ltd.) was used Electron Microscopic Observation of Stent Surface As for each of the samples of Example 2 and Comparative Example 2 below, the stent surface was observed using a scanning electron microscope (SEM) before expansion, after expansion to an inner diameter of 3 mm, and after 28 days of immersion in the simulated plasma solution.

Observation of Stent Implanted in Pig Coronary Arteries

As for each of the samples of Example 2 immersion Comparative Example 2, the stent cross section was observed using an optical interference tomographic meter (OCT) immediately after implantation in pig coronary artery and at 28 days after implantation in pig coronary artery.

Evaluation of Recoil Value of Stent at 28 Days After Implantation

In the OCT observation, a stent inner area (lumen area) represented by "a" immediately after implantation and a stent inner area represented by "b" at 28 days after implantation were measured. A reduction rate (recoil value) relative to the stent inner area immediately after implantation was calculated by the following formula.

Recoil Value=$(a-b)/a$

Example 1

A core structure comprising the above-described stent scaffold was immersed in a 27 M hydrofluoric-acid aqueous solution (2 mL) and reciprocally moved at a rate of 100 rpm. Then, the stent was taken out after 24 hours, and subjected to ultrasonic cleaning sufficiently with water and acetone followed by drying the core structure for 24 hours at 60° C. under vacuum to prepare a core structure on which a first corrosion resistant layer (thickness: 1 μm) was formed. A parylene C layer having a thickness of 100 nm was formed on this structure by CVD process so as to form a second corrosion resistant layer. Onto the parylene C surface of the structure, a first cover layer containing 400 μg of a first polymer PCL was spray-coated, and then a second cover layer containing 150 μg of a second polymer PDLLA and 100 μg of sirolimus was spray-coated so as to obtain a stent sample shown in FIG. 1.

Example 2

A core structure comprising the above-described stent scaffold was immersed in a 27 M hydrofluoric-acid aqueous solution (2 mL) and reciprocally moved at a rate of 100 rpm. Then, the stent was taken out after 24 hours, and subjected to ultrasonic cleaning sufficiently with water and acetone followed by drying the core structure for 24 hours at 60° C. under vacuum to prepare a core structure on which a first corrosion resistant layer (thickness: 1 μm) was formed. A parylene C layer having a thickness of 500 nm was formed on this structure by CVD process so as to form a second corrosion resistant layer. Onto the parylene C surface of the structure, a first cover layer containing 400 μg of a first polymer PCL was spray-coated, and then a second cover layer containing 150 μg of a second polymer PDLLA and 100 μg of sirolimus was spray-coated so as to obtain a stent sample shown in FIG. 1.

Comparative Example 1

A (non-fluorinated) core structure having an above-described stent scaffold was prepared as a stent sample.

Comparative Example 2

Figure 7:
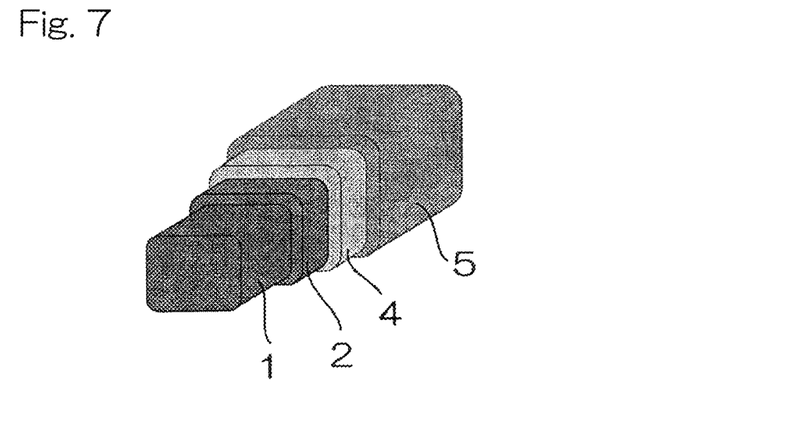
FIG. 7 shows a schematic view illustrating constituents of a stent of Comparative Example 2.

A core structure comprising the above-described stent scaffold was immersed in a 27 M hydrofluoric-acid aqueous solution (2 mL) and reciprocally moved at a rate of 100 rpm. Then, the stent was taken out after 24 hours, and subjected to ultrasonic cleaning sufficiently with water and acetone followed by drying the core structure for 24 hours at 60° C. under vacuum to prepare a core structure on which a first corrosion resistant layer (thickness: 1 μm) was formed. Onto the first corrosion resistant layer surface of the structure, a first cover layer containing 400 μg of a first polymer PCL was spray-coated, and then a second cover layer containing 150 μg of a second polymer PDLLA and 100 μg of sirolimus was spray-coated so as to obtain a stent sample shown in FIG. 7.

Comparative Example 3

Figure 8:
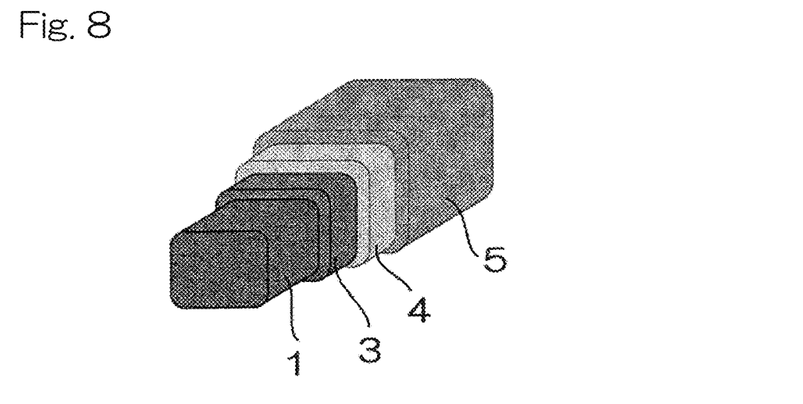
FIG. 8 shows a schematic view illustrating constituents of a stent of Comparative Example 3.

Onto a (non-fluorinated) core structure comprising the above-described stent scaffold, a parylene C layer having a thickness of 500 nm was formed by CVD process so as to form a second corrosion resistant layer. Onto the parylene C surface of the structure, a first cover layer containing 400 μg of a first polymer PCL was spray-coated, and then a second cover layer containing 150 μg of a second polymer PDLLA and 100 μg of sirolimus was spray-coated so as to obtain a stent sample shown in FIG. 8.

Table 1 shows measurement results of the weight changes in Example 1, Example 2, Comparative Example 1, Comparative Example 2 and Comparative Example 3 described above (n=5), and Table 2 shows measurement results of the radial force residual rates in the same samples. Each of the samples before immersion had a weight of 5.92±0.32 g, and each of the core structures before immersion had a radial force of 63.12±5.36 N/mm.

TABLE 1

Weight Change of Stent Samples Before and After Immersion (Weight Residual Ratio [%])

|  | Before immersion | After 28 days of immersion | (Remark) |
| --- | --- | --- | --- |
| Ex. 1 | 100 | 99.1 ± 1.3 | FIG. 1 |
| Ex. 2 | 100 | 99.3 ± 1.2 | FIG. 1 |
| Com. Ex. 1 | 100 | 79.5 ± 2.9 | FIG. 6 |
| Com. Ex. 2 | 100 | 88.3 ± 2.7 | FIG. 7 |
| Com. Ex. 3 | 100 | 88.7 ± 2.6 | FIG. 8 |

TABLE 2

Physical Property Change of Stent Samples Before and After Immersion (Radial Force Residual Ratio [%])

|  | Before immersion | After 28 days of immersion | (Remark) |
| --- | --- | --- | --- |
| Ex. 1 | 100 | 93.2 ± 3.6 | FIG. 1 |
| Ex. 2 | 100 | 94.0 ± 2.8 | FIG. 1 |
| Com. Ex. 1 | 100 | 24.5 ± 12.9 | FIG. 6 |
| Com. Ex. 2 | 100 | 81.2 ± 4.2 | FIG. 7 |
| Com. Ex. 3 | 100 | 83.1 ± 2.5 | FIG. 8 |

The samples having the constituting elements according to the present invention (Example 1, Example 2) had smaller changes in weight and radial force when compared with those of the sample without a corrosion resistant layer 2 (Comparative Example 2) and the sample without a corrosion resistant layer 1 (Comparative Example 3). Thus, it was indicated that the double layer structure of the first corrosion resistant layer and the second corrosion resistant layer provided an excellent anticorrosion effect. In contrast, the sample having none of the corrosion resistant layers (Comparative Example 1) showed considerable decrease in radial force associated with corrosion.

Table 3 shows measurement results of Mg ion elution rates in Example 2, Comparative Example 2 and Comparative Example 3 after 7, 14, 21 and 28 days of immersion as described above (n=5).

TABLE 3

Decomposition Behavior of Stent Samples Before and After Immersion (Mg Ion Elution Rate [%])

|  | After 7 days of immersion | After 14 days of immersion | After 21 days of immersion | After 28 days of immersion | (Remark) |
| --- | --- | --- | --- | --- | --- |
| Ex. 2 | 0.1 ± 0.1 | 0.5 ± 0.2 | 1.1 ± 0.2 | 1.2 ± 0.4 | FIG. 1 |
| Com. Ex. 2 | 1.8 ± 0.9 | 3.4 ± 1.4 | 5.9 ± 1.9 | 7.1 ± 3.9 | FIG. 7 |
| Com. Ex. 3 | 0.9 ± 2.5 | 3.5 ± 1.9 | 6.6 ± 2.8 | 8.9 ± 3.1 | FIG. 8 |

The samples having the constituting elements according to the present invention (Example 2) had an extremely smaller amount of Mg ions eluted over time when compared with those of the sample without a corrosion resistant layer 2 (Comparative Example 2) and the sample without a corrosion resistant layer 1 (Comparative Example 3). Thus, it was confirmed that provision of both of the first corrosion resistant layer and the second corrosion resistant layer advantageously provided a synergetic effect. That is, a desired anticorrosive effect that makes a bioabsorbable stent practically applicable cannot be obtained by providing only one of the corrosion resistant layer 2 and the corrosion resistant layer 3.

Figure 9:
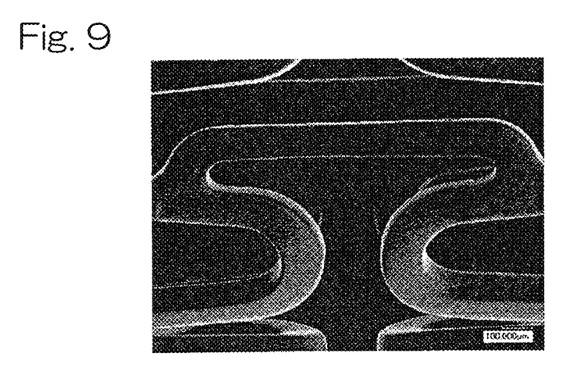
FIG. 9 is an SEM observation image of a surface of a stent according to the present invention (Example 2) before expansion.
Figure 10:
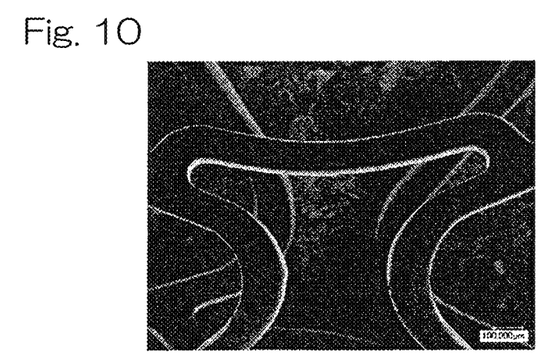
FIG. 10 is an SEM observation image of a surface of a stent according to the present invention (Example 2) after expansion.
Figure 11:
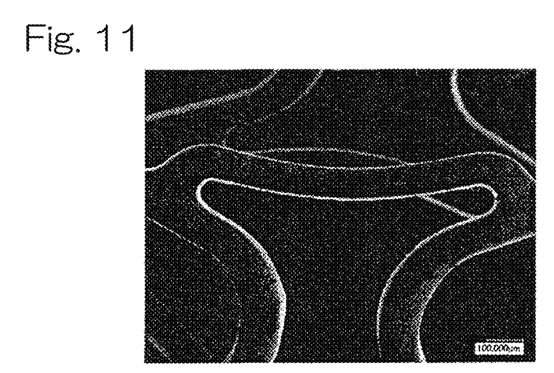
FIG. 11 is an SEM observation image of a surface of a stent according to the present invention (Example 2) after 28 days of immersion in a simulated plasma solution (EMEM+ 10% FBS)
Figure 12:
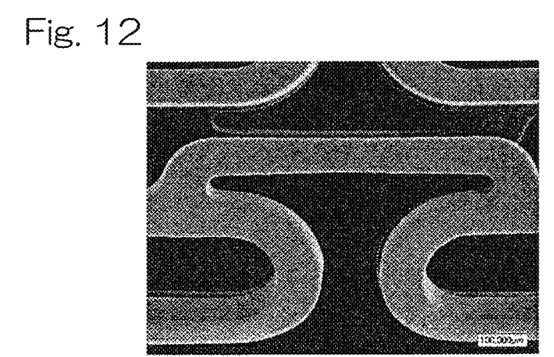
FIG. 12 is an SEM observation image of a surface of a stent of Comparative Example 2 before expansion.
Figure 13:
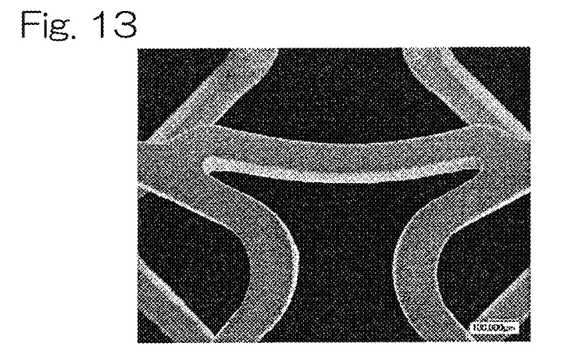
FIG. 13 is an SEM observation image of a surface of a stent of Comparative Example 2 after expansion.
Figure 14:
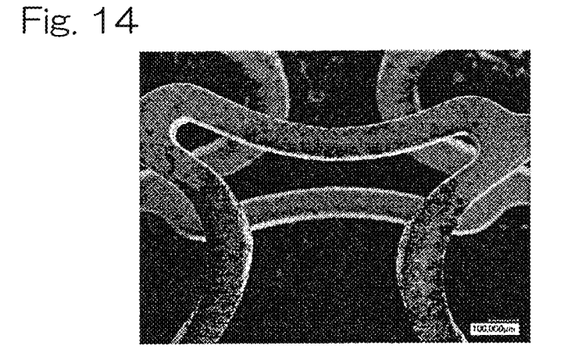
FIG. 14 is an SEM observation image of a surface of a stent of Comparative Example 2 after 28 days of immersion in the simulated plasma solution.

FIG. 9 to FIG. 14 show results of SEM observation of each stent surface of the samples of Example 2 and Comparative Example 2 before expansion, after expansion, and after 28 days of immersion in the simulated plasma solution. FIG. 9 to FIG. 11 show the stent surfaces of the samples of Example 2 before expansion (FIG. 9), after expansion (FIG. 10), and after 28 days of immersion in the simulated plasma solution (FIG. 11). FIG. 12 to FIG. 14 show the stent surfaces of the samples of the Comparative Example 2 before expansion (FIG. 12), after expansion (FIG. 13), and after 28 days of immersion in the simulated plasma solution (FIG. 14). There seems to be no difference between the stent surfaces of the samples of Example 2 before expansion, after expansion, and after 28 days of immersion in the simulated plasma solution. In contrast, the samples of Comparative Example 2 showed that corrosion proceeded mainly at locations where stress was concentrated at 28 days of immersion in the simulated plasma solution.

Figure 15:
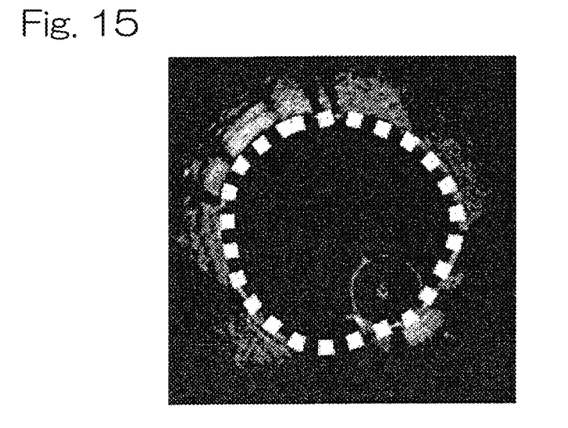
FIG. 15 is an OCT observation image of a cross section of a stent according to the present invention (Example 2) immediately after implantation in pig coronary artery.
Figure 16:
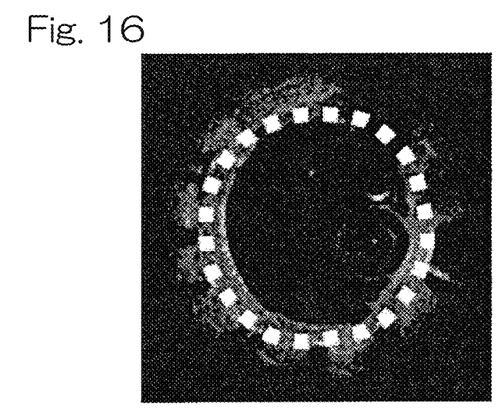
FIG. 16 is an OCT observation image of a cross section of a stent according to the present invention (Example 2) after 28 days of detention in pig coronary artery.
Figure 17:
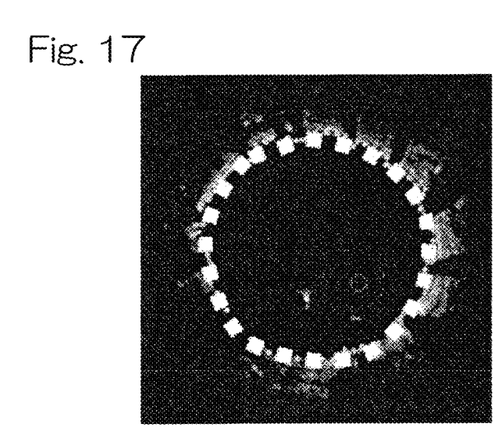
FIG. 17 is an OCT observation image of a cross section of a stent of Comparative Example 2 immediately after implantation in pig coronary artery.
Figure 18:
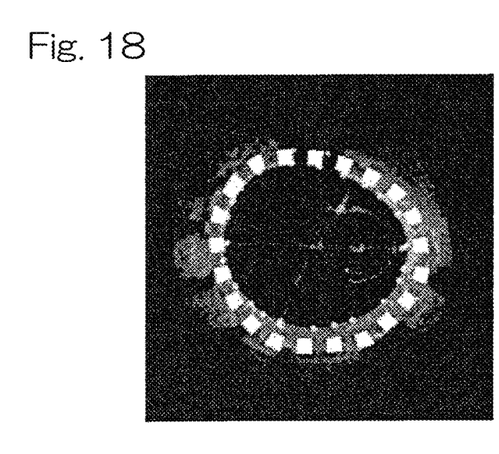
FIG. 18 is an OCT observation image of a cross section of a stent of Comparative Example 2 after 28 days of detention in pig coronary artery.

As for the respective samples of Example 2 and Comparative Example 2, OCT observation images of cross sections of pig coronary arteries immediately after stent implantation and at 28 days after stent implantation are shown in FIG. 15 (Example 2 immediately after implantation), FIG. 16 (Example 2 at 28 days after implantation), FIG. 17 (Comparative Example 2 immediately after implantation), FIG. 18 (Comparative Example 2 at 28 days after implantation).

Recoil values of the respective stent samples of Example 2 and Comparative Example 2 were determined at 28 days after implantation in pig coronary arteries. Table 4 shows calculation results of the recoil values at 28 days after implantation relative to stent inner areas before implantation.

TABLE 4

Recoil Values of Stents at 28 Days After Implantation [%]

| | 28 days after implantation |
|---|---|
| Ex. 2 | 13 ± 4 |
| Com. Ex. 2 | 25 ± 5 |

The samples having the constituting elements according to the present invention (Example 2) had significantly smaller recoil values when compared with those of the samples without the scope of the present invention (Comparative Example 2). The obtained recoil values corresponded to the other results.

The foregoing results have revealed that the synergetic function by combination of the first corrosion resistant layer and the second corrosion resistant layer is essential to suppress corrosion of the magnesium alloy and delay decrease in mechanical strength of the stent of the present invention.

INDUSTRIAL APPLICABILITY

The present invention can provide a stent comprising a core structure comprising a magnesium alloy free of a rare earth element and aluminum and highly safe to the living body and, as well as a first corrosion resistant layer and a second corrosion resistant layer that effectively delay decrease in mechanical strength associated with accelerated corrosion of the core structure. Therefore, the present invention contributes to development of medical technology and thus has remarkable industrial applicability.

Although the preferred examples of the present invention have been described with reference to the drawings, those skilled in the art would easily arrive at various changes and modifications in view of the specification and drawings without departing from the scope of the invention. Accordingly, such changes and modifications are included within the scope of the present invention.

REFERENCE NUMERALS

1 . . . Core structure (magnesium alloy)
2 . . . First corrosion resistant layer (magnesium fluoride layer)
3 . . . Second corrosion resistant layer (parylene layer)
4 . . . Biodegradable resin layer
5 . . . Biodegradable resin layer (containing a medicine)

What is claimed is:

1. A bioabsorbable stent comprising:
a core structure comprising a magnesium alloy containing 90 wt % or more of magnesium as a main component, and zinc, zirconium, and manganese as accessary components, the magnesium alloy being free of any rare earth elements and aluminum;
a first corrosion resistant layer formed on the core structure of the magnesium alloy and containing magnesium fluoride as a main component; and
a second corrosion resistant layer formed on the first corrosion resistant layer and comprising a parylene,
wherein in the magnesium alloy, unavoidable impurities selected from the group consisting of Fe, Ni, Co, and Cu are contained in a total content of 30 ppm or less, and
the magnesium alloy comprises 0.95 to 2.00 wt % of zinc, 0.05 to 0.80 wt % of zirconium, 0.05 to 0.40 wt % of manganese, and the balance consisting of magnesium and unavoidable impurities.

2. The bioabsorbable stent according to claim 1, wherein the first corrosion resistant layer is formed by performing fluorination to a surface of the magnesium alloy.

3. The bioabsorbable stent according to claim 1, wherein the first corrosion resistant layer has a layer thickness from 0.5 to 1.5 μm.

4. The bioabsorbable stent according to claim 1, wherein the second corrosion resistant layer comprises a parylene N (chemical formula 1 below), a parylene C (chemical formula 2 below), a parylene M (chemical formula 3 below), a parylene F (chemical formula 4 below), a parylene D (chemical formula 5 below), or a parylene HT (chemical formula 6 below).

(1)

(2)

-continued (3)
(4)
(5)
(6)

5. The bioabsorbable stent according to claim 1, wherein the second corrosion resistant layer has a layer thickness from 0.05 to 1 μm.

6. The bioabsorbable stent according to claim 1, wherein on at least a part of the second corrosion resistant layer surface, a biodegradable polymer layer is formed.

7. The bioabsorbable stent according to claim 6, wherein the biodegradable polymer is an aliphatic polyester.

8. The bioabsorbable stent according to claim 6, wherein the biodegradable polymer layer contains an intimal thickening inhibitor.

9. The bioabsorbable stent according to claim 8, wherein the inhibitor is a limus drug.

10. A method for producing a bioabsorbable stent including a core structure comprising a magnesium alloy containing 90 wt % or more of magnesium as a main component, and zinc, zirconium, and manganese as accessary components, the magnesium alloy being free of any rare earth elements and aluminum, the method comprising:

preparing the core structure comprising the magnesium alloy;

electropolishing the core structure and performing fluorination to a surface of the electropolished core structure so as to form a first corrosion resistant layer containing magnesium fluoride as a main component; and vapor depositing a paraxylylene resin on the first corrosion resistant layer so as to form a second corrosion resistant layer comprising a parylene, wherein in the magnesium alloy, unavoidable impurities selected from the group consisting of Fe, Ni, Co, and Cu are contained in a total content of 30 ppm or less, and the magnesium alloy comprises 0.95 to 2.00 wt % of zinc, 0.05 to 0.80 wt % of zirconium, 0.05 to 0.40 wt % of manganese, and the balance consisting of magnesium and unavoidable impurities.

* * * * *